United States Patent
Granados-Covarrubias et al.

(10) Patent No.: US 9,580,406 B2
(45) Date of Patent: Feb. 28, 2017

(54) PROCESSES FOR THE PREPARATION OF AXITINIB

(71) Applicant: Signa S.A. de C.V., Toluca (MX)

(72) Inventors: Evin Hazael Granados-Covarrubias, Toluca de Lerdo (MX); José Miguel Lazcano-Seres, Calimaya (MX); Roberto Carlos Melgar-Fernández, Metepec (MX); Armando Zambrano-Huerta, Zinacantepec (MX); Martín Raúl Montiel-Pérez, Toluca (MX); Israel Flores-García, Toluca (MX)

(73) Assignee: Signa S.A. de C.V., Toluca (MX)

( * ) Notice: Subject to any disclaimer, the term of this patent is extended or adjusted under 35 U.S.C. 154(b) by 0 days.

(21) Appl. No.: 15/139,494

(22) Filed: Apr. 27, 2016

(65) Prior Publication Data

US 2016/0318898 A1 Nov. 3, 2016

Related U.S. Application Data

(60) Provisional application No. 62/153,743, filed on Apr. 28, 2015.

(51) Int. Cl.
*C07D 401/06* (2006.01)

(52) U.S. Cl.
CPC ........ *C07D 401/06* (2013.01); *C07B 2200/13* (2013.01)

(58) Field of Classification Search
CPC .................................................. C07D 401/06
USPC ........................................................ 546/275.7
See application file for complete search history.

(56) References Cited

U.S. PATENT DOCUMENTS

| 7,232,910 B2 | 6/2007 | Ewanicki et al. |
| 2009/0062347 A1 | 3/2009 | Czarnik |

FOREIGN PATENT DOCUMENTS

| CN | 103570696 A | | 2/2014 |
| WO | 0102369 A2 | | 1/2001 |
| WO | 2006/048745 | * | 5/2006 |
| WO | 2006048745 A1 | | 5/2006 |

OTHER PUBLICATIONS

Zhai et ., "Effective Laboratory, etc.," Org. Process Res. Dev. 2015,19, 849-857.*
Chekal et al., "Development of an Efficient Pd-Catalyzed Coupling Process for Axitinib," Organic Process Research & Development, 2014, pp. 266-274, vol. 18, No. 1, American Chemical Society.
Flahive et al., "Development of an Effective Palladium Removal Process for VEGF Oncology Candidate AG13736 and a Simple, Efficient Screening Technique for Scavenger Reagent Identification," Organic Process Research & Development, 2008, pp. 637-645, vol. 12, No. 4, American Chemical Society.

* cited by examiner

*Primary Examiner* — Patricia L Morris
(74) *Attorney, Agent, or Firm* — The Webb Law Firm

(57) ABSTRACT

Processes for the preparation of Axitinib in good yield (generally greater than 80%) are provided that avoid the use of a palladium-catalyzed coupling reaction.

17 Claims, No Drawings

PROCESSES FOR THE PREPARATION OF AXITINIB

CROSS-REFERENCE TO RELATED APPLICATION

This application claims the benefit of U.S. Provisional Patent Application No. 62/153,743 filed Apr. 28, 2015, the disclosure of which is hereby incorporated in its entirety by reference.

TECHNICAL FIELD

The present invention relates to the field of chemical synthesis of organic compounds and, in particular, to a process for the synthesis of Axitinib.

BACKGROUND

Axitinib (1) is a vascular endothelial growth factor (VEGF) inhibitor. These kinds of antagonists have been recognized as an important class of pharmaceutical agents for development due to their efficiency in controlling the growth and proliferation of cancer cells. INLYTA®, containing Axitinib as its active ingredient, was approved by the Food and Drug Administration (FDA) in 2012 for the treatment of patients with advanced renal cell carcinoma (RCC).

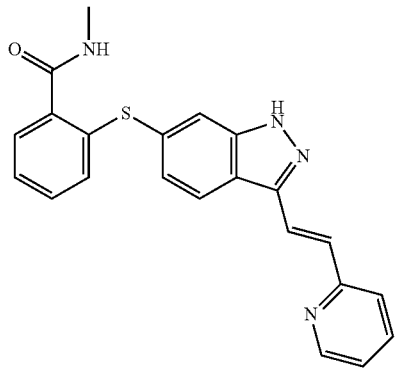

Axitinib (1)

WO 01/02369 A2 describes indazole compounds that modulate and/or inhibit the activity of certain protein kinases. These compounds, and pharmaceutical compositions containing them, are capable of mediating tyrosine kinase signal transduction and thereby modulate and/or inhibit unwanted cell proliferation. The invention is also directed to the therapeutic or prophylactic use of pharmaceutical compositions containing such compounds, and to methods of treating cancer and other disease states associated with unwanted angiogenesis and/or cellular proliferation, such as diabetic retinopathy, neovascular glaucoma, rheumatoid arthritis, and psoriasis, by administering effective amounts of such compounds.

U.S. Pat. No. 7,232,910 B2 relates to methods for preparing indazole compounds, which are useful as modulators and/or inhibitors of protein kinases. U.S. Pat. No. 7,232,910 also relates to intermediate compounds useful in the preparation of such compounds.

WO 2006/048745 A1 relates to methods for preparing indazole compounds or pharmaceutically acceptable salts or solvates thereof. Such compounds are useful as anti-angiogenesis agents and as agents for modulating and/or inhibiting the activity of protein kinases, thus providing treatments for cancer or other diseases associated with cellular proliferation mediated by protein kinases.

Org. Process Res. Dev., 2008, 12(4), 637-645 describes that AG13736 (Axitinib), an inhibitor of vascular endothelial growth factor (VEGF) under investigation as an oncology drug, is currently manufactured via a three-step process that utilizes two palladium-mediated cross-couplings. Historically, removal of residual heavy metals from the active pharmaceutical ingredient has been a persistent issue. The development of a much improved process for palladium removal and a useful screening technique developed to rapidly identify the most efficient reagents for this purpose are outlined. The performance of the new endgame process in pilot-plant scale-up is also discussed.

US 2009/062347 A1 describes deuterium-enriched Axitinib, pharmaceutically acceptable salt forms thereof, and methods of treating using the same.

Org. Process Res. Dev., 2014, 18 (1), 266-274 describes a manufacturing process of Axitinib involving two Pd-catalyzed coupling reactions, a Migita coupling and a Heck reaction. Optimization of both of these pivotal bond-formation steps is discussed, as well as approaches to control the impurities present in the prepared Axitinib. Essential to the control strategy was the optimization of the Heck reaction to minimize formation of impurities, in addition to the development of an efficient isolation of crude Axitinib to purge impurities.

CN 103570696 relates to a method for preparing an intermediate of Axitinib and the application of this intermediate in the preparation of Axitinib. The preparation method for the intermediate of Axitinib, 3-iodo-6-nitro-1-(tertrahydro-2H-pyran-2-yl)-1H-indazole, comprises the following steps: first, 6-nitroindazole and 3,4-dihydro-2H-pyran are reacted under the action of a catalyst to protect the indazole at its N—H site; and, second, the iodination occurs at the 3-position. The intermediate may then be used in the preparation of Axitinib as follows: first, a Heck coupling reaction is carried out on the intermediate with 2-vinyl pyridine; second, the 6-nitro group is reduced and converted to an iodo group; and finally, Axitinib is obtained after the docking of 2-sulfydryl-N-methyl benzamide at the 6-position and deprotection of the indazole nitrogen. The initial raw materials for the process are available commercially and the method provides a high yield and high molecule economic efficiency, is efficient, environment-friendly, and is suitable for industrial mass production. However, the process of CN 103570696 still relies on the use of palladium-catalyzed reactions, which necessitates removal of the palladium before the product can be used as a pharmaceutical.

SUMMARY

This invention is based, at least in part, on processes for preparing Axitinib in good yield (generally greater than 80%) without requiring the use of palladium-catalyzed coupling reactions. Methods of the present invention may also provide the use of nearly stoichiometric quantities of economical, safe and easy to handle reagents and a product that may be easily isolatable.

In a first aspect of the present invention there is provided a process for the preparation of a compound of Formula (1):

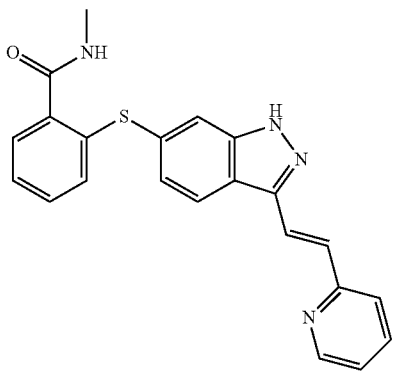

the process comprising:
(i) coupling, in the presence of a first base, a copper (I) catalyst and a ligand in a first solvent, a compound of Formula (2):

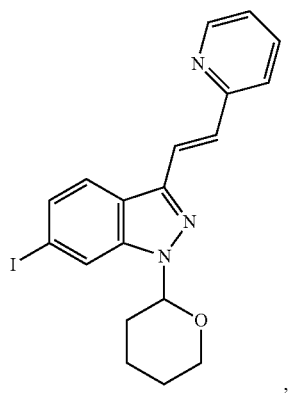

with a compound of Formula (3):

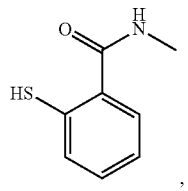

thereby forming a compound of Formula (4):

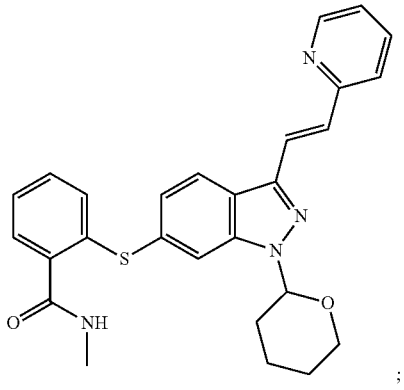

and
(ii) converting the compound of Formula (4) to Axitinib.

In a preferred embodiment of the first aspect, the copper (I) catalyst is copper (I) iodide.

In one preferred embodiment of the first aspect, the ligand is selected from the group consisting of ethanoldiamine, salicyladehyde, N,N-dimethylglycine, 1,10-phenanthroline and o-phenylenediamine. Most preferably, the ligand is o-phenylenediamine.

In another preferred embodiment of the first aspect, the first solvent is N,N-dimethylformamide.

In a further preferred embodiment of the first aspect, the first base is potassium hydroxide.

In yet another preferred embodiment of the first aspect, the coupling reaction is carried out at a temperature of between about 90° C. and about 125° C. Most preferably, the coupling is carried out at a temperature of about 120° C.

In a second aspect of the present invention there is provided the process of the first aspect further comprising crystallizing the compound of Formula (4) using a co-solvent.

In one preferred embodiment of the second aspect, the co-solvent is ethyl acetate.

In a further preferred embodiment of the second aspect, the compound of Formula (4) is crystallized using ethyl acetate with water or a mixture of water and ammonium hydroxide.

In a third aspect of the present invention there is provided the process of the first aspect wherein the converting of a compound of Formula (4) to a compound of Formula (1) comprises treating the compound of Formula (4) with a first acid in a second solvent.

In a preferred embodiment of the third aspect, the first acid is selected form the group consisting of organic sulfonic acids, trifluoroacetic acid, phosphorous oxoacids, sulfuric acid and Lewis acids. Most preferably, the first acid is p-toluene sulfonic acid.

In a further illustrative embodiment of the present invention is provided a composition comprising Axitinib and copper.

Another illustrative embodiment of the present invention provides a composition comprising Axitinib and a compound of Formula (5):

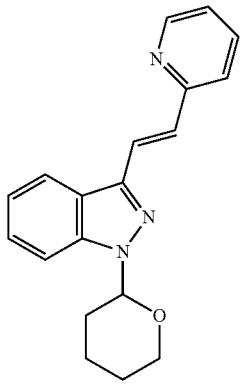

Other aspects and features of the present invention will become apparent to those ordinarily skilled in the art upon review of the following description of specific embodiments of the invention in conjunction with the accompanying figures.

DETAILED DESCRIPTION

As used herein, the terms "coupling" and "coupling reaction" refer to a variety of reactions where two hydrocarbon fragments are joined covalently with the aid of a metal catalyst.

As used herein the terms "halide", "halogen" and "halo" refer to fluoro, chloro, bromo, or iodo substituents.

As used herein the term "ligand" refers to an ion or molecule that binds to a central metal atom to form a coordination complex. Examples of ligands include but are not limited to, ethanoldiamine, salicylaldehyde, N,N-dimethylglycine, ethylene glycol and o-phenylenediamine.

As used herein, the terms "protect", "protected" and "protecting" refer to a process in which a reactive functional group in a chemical compound is selectively masked through the formation of a non-reactive functional group in order to allow a selective reaction to occur elsewhere on said chemical compound under a given set of conditions. Such non-reactive functional groups are herein named "protecting groups". The term "suitable protecting group", as used herein refers to those protecting groups that are useful in the preparation of a compound of the present invention. Non-limiting examples of suitable protecting groups include tetrahydropyranyl acetal (THP), [2-(trimethylsilyl)ethoxy]methylacetal (SEM), and tert-butoxycarbamate (BOC).

As used herein, the term "volumes" and the abbreviated term "vol." refer to the parts of solvent or liquids by volume (mL) with respect to the weight of solute (g). For example, when an experiment is conducted using 1 g of starting material and 100 mL of solvent, it is said that 100 volumes of solvent are used.

As used herein, the term "eq." corresponds with "equivalents" and refers to the molar equivalents of the subject component with respect to the raw material in the step, which is assigned as 1.0 equivalent.

As used herein, the term "pure" means, unless otherwise stated, substantially free from impurities. Generally, compounds of the present invention are at least 75% pure (w/w), greater than about 90% pure (w/w), or greater than about 95% pure (w/w).

The use of "about" when describing the embodiments of the present invention refers to the common variance to a given amount or condition that would be understood or expected by the person skilled in the art to provide substantially the same result. For example, when used with respect to temperature, "about" refers to an allowable variance of ±5° C. When used with respect to purity and molar equivalents, "about" refers to an allowable variance of ±10% of the stated value. When used with respect to time, "about" refers to an allowable variance of ±10 minutes when the time is one or two hours, and ±1 hour when longer periods of time are referenced.

According to one aspect of the present invention, there is provided a process for the preparation of Axitinib (1)

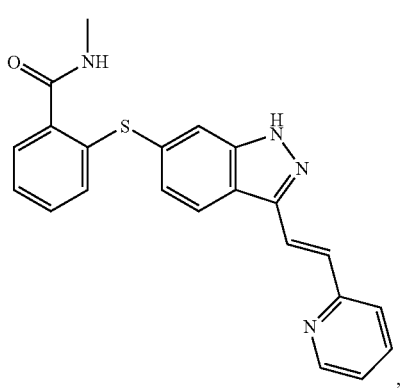

the process comprising:

(i) coupling, in the presence of a first base, a copper (I) catalyst and a ligand in a first solvent, a compound of Formula (2):

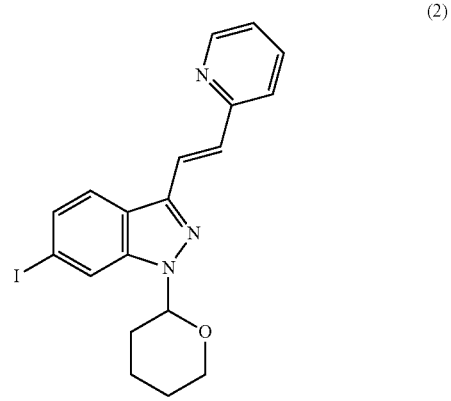 [SMILES: Ic1ccc2c(/C=C/c3ccccn3)nn(C3CCCCO3)c2c1]

with a compound of Formula (3):

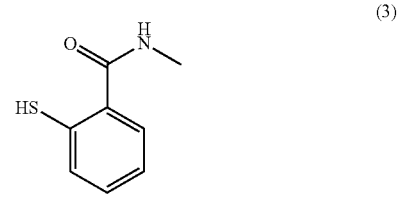

thereby forming a compound of Formula (4):

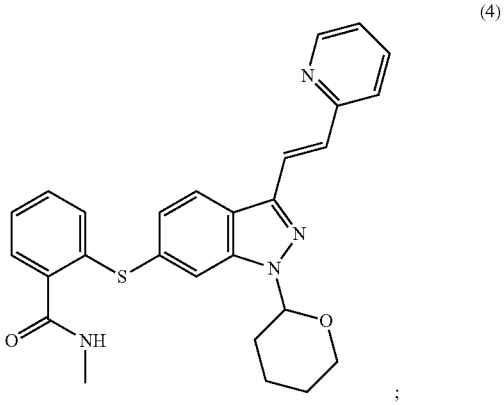 [SMILES: CNC(=O)c1ccccc1Sc1ccc2c(/C=C/c3ccccn3)nn(C3CCCCO3)c2c1]

and (ii) treating the compound of Formula (4), with a first acid in a second solvent.

This process is exemplified as set out in Scheme 1. Exemplary reagents and conditions for these reactions are also set out below.

Scheme 1

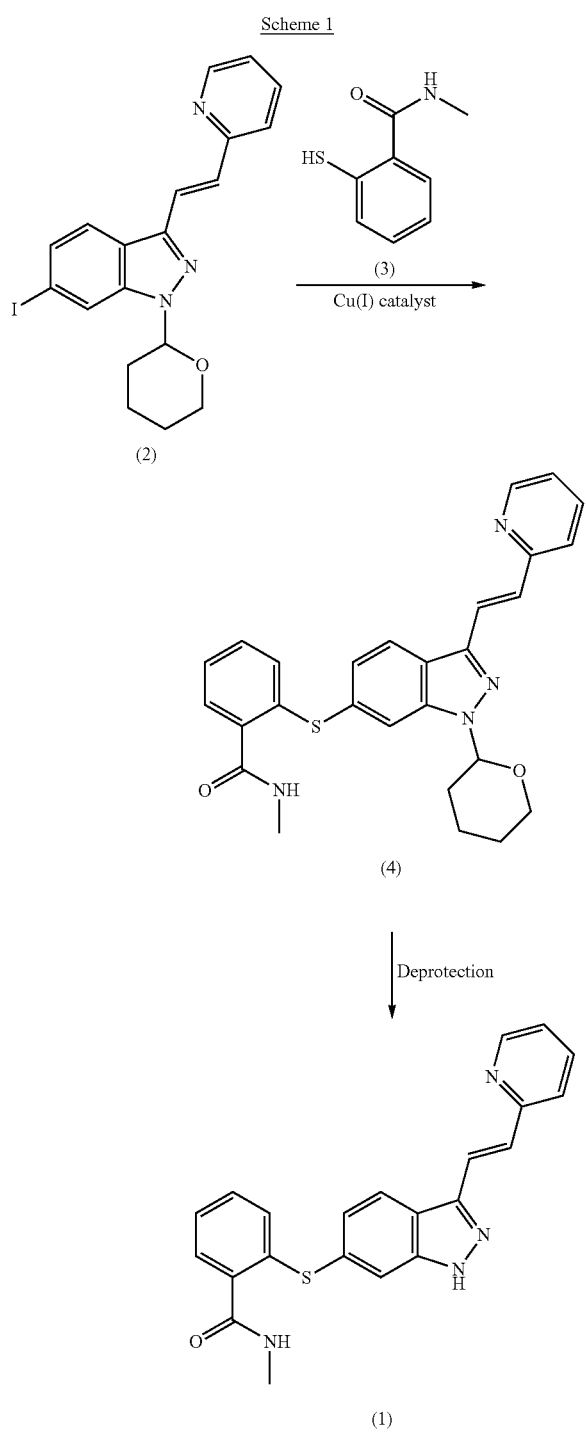

The copper (I) catalyst may be a compound of copper (I) having the formula CuX, wherein X is an organic or inorganic monovalent anion. An inorganic anion may be, for example, a halide. CuX with an organic anion may be, for example, copper (I) acetylide, lithium dimethylcuprate, lithium diphenylcuprate, pentamesitylpentacopper, or (η-cyclopentadienyl triethylphosphine)copper. A preferred copper (I) catalyst is copper (I) iodide (CuI). The catalyst may be used in amounts of from about 0.05 molar equivalents to about 0.2 molar equivalents with respect to the compound of Formula (2).

The ligand may be selected from the group consisting of ethanoldiamine, salicyladehyde, N,N-dimethylglycine, 1,10-phenanthroline and o-phenylenediamine. A preferred ligand is o-phenylenediamine, with a preferred ratio of ligand with respect to the catalyst being 1:1 or 2:1, most preferably, 2:1.

The reaction of the compound of Formula (2) with the compound of Formula (3) may be conducted in a first solvent and may be performed at a temperature ranging from about room temperature to the boiling point of the first solvent. Preferably, the reaction is conducted at a temperature of between 90° C. and 125° C.

The first base may be inorganic or organic, and is preferably selected from the group consisting of metal hydroxides, carbonates, phosphates, tertiary amines, and aryl amines. Preferred examples of the first base are sodium hydroxide and potassium hydroxide. Other suitable examples of the first base include, but are not limited to, lithium hydroxide, sodium carbonate, sodium bicarbonate, potassium carbonate, potassium bicarbonate, lithium carbonate, cesium carbonate, potassium phosphate, sodium phosphate, triethylamine, diisopropylamine, N,N-dimethylaniline, N,N-diethylaniline, pyridine, n-butyllithium, lithium diisopropylamine (LDA) lithium hexamethyldisilazide (LiHMDS), sodium hexamethyldisilazide (NaHMDS), potassium hexamethyldisilazanide (KHMDS), sodium hydride (NaH), potassium hydride (KH), potassium tert-butoxide, and mixtures thereof. Most preferred as the first base is potassium hydroxide.

The first solvent may be an alcohol (such as, for example, isopropanol or butanol), an alkyl ether (such as, for example tetrahydrofuran or 1,4-dioxane), a ketone (such as, for example, acetone), an aromatic hydrocarbon (such as, for example, toluene or xylenes), a nitrile (such as, for example, acetonitrile, propionitrile, butyronitrile or benzonitrile), an N,N-dialkylamide (such as, for example, N,N-dimethylformamide, N,N-dimethylacetamide or N-methyl-2-pyrrolidinone), a sulfoxide (such as, for example, dimethyl sulfoxide), or a mixture thereof. Preferably, the first solvent is N,N-dimethylformamide.

The reaction of the compound of Formula (2) with the compound of Formula (3) in the presence of the first base, the copper catalyst and the ligand in a first solvent may be crystallized by addition to the crude reaction mixture of a suitable co-solvent.

The co-solvent may be a suitable protic or aprotic organic solvent. Preferably, the co-solvent is an alcohol (such as, for example, isopropanol or butanol), an alkyl ether (such as, for example tetrahydrofuran or 1,4-dioxane), a ketone (such as, for example, acetone), a carboxylic ester (such as, for example, ethyl acetate or isopropyl acetate), an aromatic hydrocarbon (such as, for example, toluene or xylenes), a nitrile (such as, for example, acetonitrile, propionitrile, butyronitrile or benzonitrile), a N,N-dialkylamide (such as, for example, N,N-dimethylformamide, N,N-dimethylacetamide or N-methyl-2-pyrrolidinone), a sulfoxide (such as, for example, dimethyl sulfoxide), or a mixture thereof. A preferred co-solvent is ethyl acetate, particularly when the first solvent is N,N-dimethylformamide.

For the deprotection of the compound of Formula (4) to provide Axitinib (1), the first acid may be an organic or inorganic acid selected from the group consisting of organic sulfonic acids (such as, for example, p-toluenesulfonic acid, camphorsulfonic acid and methansulfonic acid), trifluoroacetic acid, phosphorous oxoacids (such as, for example, phosphoric acid, phosphorous acid or hypophosphorous acid), sulfuric acid and Lewis acids (such as, for example, SnCl$_4$, TiCl$_4$, BF$_3$.OEt$_2$). Preferably, the first acid is p-toluenesulfonic acid or methansulfonic acid.

When deprotecting the compound of Formula (4), the second solvent may be selected from the group consisting of alcohols (such as, methanol, isopropanol or butanol), alkyl ethers (such as, for example, tetrahydrofuran or 1,4-dioxane), ketones (such as, for example, acetone), aromatic hydrocarbons (such as, for example, toluene or xylenes), nitriles (such as, for example, acetonitrile, propionitrile, butyronitrile or benzonitrile), a N,N-dialkylamide (such as, for example, N,N-dimethylformamide, N,N-dimethylacetamide or N-methyl-2-pyrrolidonone), a sulfoxide (such as, for example, dimethyl sulfoxide), or a mixture thereof. Preferably, the second solvent is methanol.

EXAMPLES

The following examples are illustrative of some of the embodiments of the invention described herein. These examples do not limit the spirit or scope of the invention in any way.

Example 1

Under positive nitrogen pressure, in a first flask, 2-mercapto-N-methylbenzamide (1.94 g, 1.0 eq.) was dissolved in N,N-dimethylformamide (10 mL, 2 vol.). The temperature was adjusted to about 60° C., potassium hydroxide (0.98 g, 1.50 eq.) was added, and the mixture was stirred for 1 hour at about 60° C. Copper (I) iodide (0.11 g, 0.05 eq.) and o-phenylenediamine (0.13 g, 0.10 eq.) were then added and the mixture was stirred for about 1 hour at about 60° C. In a second flask, (E)-6-iodo-3-(2-(pyridin-2-yl)vinyl)-1-(tetrahydro-2H-pyran-2-yl)-1H-indazole (5.0 g, 1.0 eq.) was dissolved in N,N-dimethylformamide (35 mL, 7 vol.) and the temperature was adjusted to about 60° C. The contents of the second flask were then added to the contents of the first flask and the temperature was increased to about 90° C. Reaction completion was monitored by Thin Layer Chromatography (TLC). After reaction completion, the solution was cooled to about 35° C., ethyl acetate (12.5 mL, 2.5 vol.) and water (50 mL, 10 vol.) were added, and the mixture was adjusted to about 25° C. and allowed to stir for 1 hour. The suspension was filtered and the filter cake was washed with water (25 mL, 5 vol.) and dried at about 45° C. under vacuum for 16 hours to afford (E)-N-methyl-2-((3-(2-(pyridin-2-yl)vinyl)-1-(tetrahydro-2H-pyran-2-yl)-1H-indazol-6-yl)thio)benzamide (4.07 g, 81.4% weight yield).

Example 2

The dried solid obtained in Example 1 was added into a flask with methanol (20 mL, 4 vol.) and p-toluenesulfonic acid (4.28 g, 2 eq.), and then heated at reflux for about 4 hours. After cooling, the resulting solid was isolated by filtration and washed with methanol (20 mL, 4 vol.) and water (20 mL, 4 vol.) to afford Axitinib (3.87 g, 95.1% weight yield).

Example 3

Under positive nitrogen pressure, in a first flask, 2-mercapto-N-methylbenzamide (3.88 g, 1.0 eq.) was dissolved in N,N-dimethylformamide (20 mL, 2 vol.). After the temperature of the solution was adjusted to about 60° C., potassium hydroxide (1.95 g, 1.50 eq.) was added, and the mixture was stirred for 1 hour at about 60° C. Copper (I) iodide (0.22 g, 0.05 eq.) and o-phenylenediamine (0.26 g, 0.10 eq.) were added and stirred for about 1 hour at about 60° C. In a second flask, (E)-6-iodo-3-(2-(pyridin-2-yl)vinyl)-1-(tetrahydro-2H-pyran-2-yl)-1H-indazole (10.0 g, 1.0 eq.) was dissolved in N,N-dimethylformamide (70 mL, 7 vol.) and warmed to about 60° C. The contents of the second flask were then added to the first flask and the temperature was adjusted to about 100° C. Reaction completion was monitored by TLC. After reaction completion, the solution was cooled to about 30° C. and maintained for about 10 hours. Ethyl acetate (25 mL, 2.5 vol.) and water (100 mL, 10 vol.) were added, the temperature was adjusted to about 20° C. and allowed to stir for 1 hour. The resulting suspension was filtered and the filter cake was washed with water (50 mL, 5 vol.) and dried at about 45° C. under vacuum for 16 hours to afford (E)-N-methyl-2-((3-(2-(pyridin-2-yl)vinyl)-1-(tetrahydro-2H-pyran-2-yl)-1H-indazol-6-yl)thio)benzamide (8.42 g, 84.2% yield).

Example 4

Under positive nitrogen pressure, in a first flask, 2-mercapto-N-methylbenzamide (1.94 g, 1.0 eq.) was dissolved in N,N-dimethylformamide (10 mL, 2 vol.). The temperature of the solution was adjusted to about 60° C., potassium hydroxide (0.98 g, 1.50 eq.) was added, and the mixture was stirred for 1 hour at about 60° C. Copper (I) iodide (0.11 g, 0.05 eq.) and o-phenylenediamine (0.13 g, 0.10 eq.) were added and the mixture was stirred for about 1 hour at about 60° C. In a second flask, (E)-6-iodo-3-(2-(pyridin-2-yl)vinyl)-1-(tetrahydro-2H-pyran-2-yl)-1H-indazole (5.0 g, 1.0 eq.) was dissolved in N,N-dimethylformamide (35 mL, 5 vol.) and the temperature was adjusted to about 60° C. The contents of the second flask were then added to the first flask and the temperature was then increased to about 120° C. Reaction completion was monitored by TLC. After reaction completion, the solution was cooled to about 35° C., ethyl acetate (12.5 mL, 2.5 vol.) and water (50 mL, 10 vol.) were added, the temperature was adjusted to about 25° C., and allowed to stir for 1 hour. The resulting suspension was filtered and the filter cake was washed with water (25 mL, 5 vol.) and dried at about 45° C. under vacuum for 16 hours to afford (E)-N-methyl-2-((3-(2-(pyridin-2-yl)vinyl)-1-(tetrahydro-2H-pyran-2-yl)-1H-indazol-6-yl)thio)benzamide (4.36 g, 87.2 weight yield).

Example 5

Under positive nitrogen pressure, in a first flask, 2-mercapto-N-methylbenzamide (72.51 g, 1.0 eq.) was dissolved in N,N-dimethylformamide (108.7 mL, 1.5 vol.). The temperature was adjusted to about 60° C., potassium hydroxide (37.47 g, 1.54 eq.) was added, and the mixture was stirred for 1 hour at about 60° C. Copper (I) iodide (41.29 g, 0.5 eq.) and o-phenylenediamine (46.89 g, 1.0 eq.) were added and the mixture was stirred for about 1 hour at about 60° C. In a second flask, (E)-6-iodo-3-(2-(pyridin-2-yl)vinyl)-1-(tetrahydro-2H-pyran-2-yl)-1H-indazole (187.0 g, 1.0 eq., corrected by assay) was dissolved in N,N-dimethylformamide (1309 mL, 7 vol.), and the temperature was adjusted to about 70° C. The contents of the second flask were then added to the contents of the first flask and the temperature was increased to about 120° C. Reaction completion was monitored by Thin Layer Chromatography (TLC). After reaction completion, the solution was cooled to about 25° C., ethyl acetate (374 mL, 2 vol.) and a mixture of water (1496 mL, 8 vol.) and ammonium hydroxide (374 mL, 2 vol.) were added, and the mixture was allowed to stir for 1 hour. The resulting suspension was filtered and the filter cake was washed with water (935 mL, 5 vol., twice) and dried at about 65° C. under vacuum for 16 hours to afford (E)-N-methyl-2-((3-(2-(pyridin-2-yl)vinyl)-1-(tetrahydro-2H-pyran-2-yl)-1H-indazol-6-yl)thio)benzamide (152 g, 81% weight yield) as crude material. In a third flask, the crude material (150 g) was dissolved in dichloromethane (3450 mL, 23 vol.) and heated until dissolution at 30° C. Charcoal was added to the solution and the dispersion was stirred for 1 hour at 30° C. The dispersion was filtered and washed with dichloromethane (300 mL, 2.0 vol.), following which the volume of the solution was reduced to 5 vol. by distillation. Isopropanol (1500 mL, 10 vol.) was added and the volume of the solution was again reduced to 5 vol. by distillation. Isopropanol (750 mL, 5 vol.) was added, and the mixture was heated at reflux for 2 hours. The reaction mixture was cooled to 25° C. and filtered, with the white to pale yellow solid obtained being washed with isopropanol (300 mL, 2.0 vol.) prior to drying at about 65° C. under vacuum for 16 hours to afford (E)-N-methyl-2-((3-(2-(pyridin-2-yl)vinyl)-1-(tetrahydro-2H-pyran-2-yl)-1H-indazol-6-yl)thio)benzamide (129 g, 68% weight yield).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A process for the preparation of a compound of Formula (1):

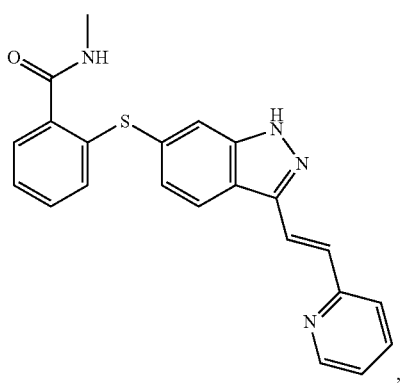

the process comprising:
(i) coupling, in the presence of a first base, a copper (I) catalyst of the formula CuX, wherein X is an organic or inorganic monovalent anion, and a ligand selected from the group consisting of ethanoldiamine, salicyladehyde, N,N-dimethylglycine, 1,10-phenanthroline and o-phenylenediamine in a first solvent, a compound of Formula (2):

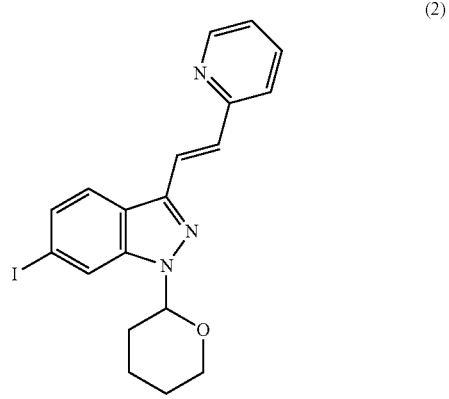 [SMILES: Ic1ccc2c(/C=C/c3ccccn3)nn(C3CCCCO3)c2c1]

with a compound of Formula (3):

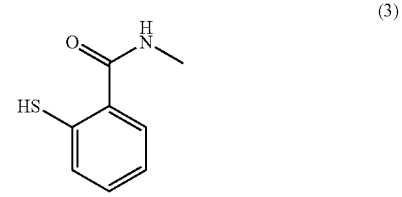

at a temperature between room temperature and the boiling point of the first solvent, thereby forming a compound of Formula (4):

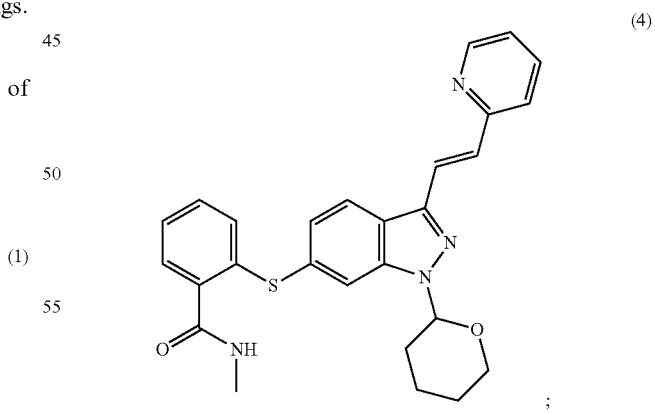

and
(ii) reacting the compound of Formula (4) with a first acid in a second solvent to form a compound of Formula (1).

2. The process of claim 1 wherein the copper (I) catalyst is copper (I) iodide.

3. The process of claim 2 wherein the ligand is o-phenylenediamine.

4. The process of claim 1 wherein the first solvent is N,N-dimethylformamide.

5. The process of claim 3 wherein the first solvent is N,N-dimethylformamide.

6. The process of claim 1 wherein the first base is potassium hydroxide.

7. The process of claim 3 wherein the first base is potassium hydroxide.

8. The process of claim 5 wherein the first base is potassium hydroxide.

9. The process of claim 1 further comprising crystallizing the compound of Formula (4) using a co-solvent.

10. The process of claim 9 wherein the co-solvent is ethyl acetate.

11. The process of claim 10 further comprising crystallizing the compound of Formula (4) using water or a mixture of water and ammonium hydroxide.

12. The process of claim 1 wherein the coupling reaction is carried out at a temperature of between 115° C. and 125° C.

13. The process of claim 3 wherein the coupling reaction is carried out at a temperature of between 90° C. and 125° C.

14. The process of claim 1 wherein the first acid is selected from the group consisting of organic sulfonic acid, trifluoroacetic acid, phosphorous oxoacids, sulfuric acid and Lewis acids.

15. The process of claim 14 wherein the first acid is p-toluene sulfonic acid.

16. The process of claim 3 wherein the first acid is selected form the group consisting of organic sulfonic acid, trifluoroacetic acid, phosphorous oxoacids, sulfuric acid and Lewis acids.

17. The process of claim 16 wherein the first acid is p-toluene sulfonic acid.

* * * * *

UNITED STATES PATENT AND TRADEMARK OFFICE
CERTIFICATE OF CORRECTION

PATENT NO. : 9,580,406 B2  
APPLICATION NO. : 15/139494  
DATED : February 28, 2017  
INVENTOR(S) : Evin Hazael Granados-Covarrubias et al.

It is certified that error appears in the above-identified patent and that said Letters Patent is hereby corrected as shown below:

In the Claims

Column 12, Lines 5-6, Claim 1, delete "salicyladehyde," and insert -- salicylaldehyde, --

Signed and Sealed this
Seventeenth Day of October, 2017

Joseph Matal
*Performing the Functions and Duties of the
Under Secretary of Commerce for Intellectual Property and
Director of the United States Patent and Trademark Office*